United States Patent [19]

Fellows et al.

[11] Patent Number: 4,639,536

[45] Date of Patent: Jan. 27, 1987

[54] INTERMEDIATE, ITS SYNTHESIS, AND ITS USE IN A PROCESS FOR THE PREPARATION OF 2,3-DIHYDRO-2,2-DIMETHYL-7-HYDROXYBENZOFURAN

[75] Inventors: Constance A. Fellows, Durham; Wallace Y. Fu, Chapel Hill, both of N.C.

[73] Assignee: Union Carbide Corporation, Danbury, Conn.

[21] Appl. No.: 645,714

[22] Filed: Aug. 30, 1984

[51] Int. Cl.$^4$ ..................... C07D 307/86; C07C 43/23
[52] U.S. Cl. ..................................... 549/462; 568/652
[58] Field of Search ......................... 549/462; 568/652

[56] References Cited

U.S. PATENT DOCUMENTS

| | | | |
|---|---|---|---|
| 3,274,260 | 9/1966 | Levy et al. | 568/650 |
| 3,474,170 | 10/1969 | Scharpf | 549/470 |
| 3,927,118 | 12/1975 | Ozretich | 568/652 |
| 4,118,400 | 10/1978 | Michaely | 549/434 |
| 4,250,333 | 2/1981 | Rakoutz | 568/652 |
| 4,252,985 | 2/1981 | Rakoutz | 568/652 |
| 4,314,086 | 2/1982 | Soula et al. | 568/652 |
| 4,321,204 | 3/1982 | Buttner et al. | 549/462 |
| 4,380,654 | 4/1983 | Franko-Fillipasic et al. | 549/462 |

FOREIGN PATENT DOCUMENTS 40400 11/1981 European Pat. Off. .
352983 7/1919 Fed. Rep. of Germany ...... 568/652
173347 of 0000 Hungary .

OTHER PUBLICATIONS

Rindfusz, J.A.C.S., vol. 41, pp. 665-670 (1919).
J. Gripenberg and T. Hase, "The Ring Opening of Aromatic O-Heterocycles by Sodium in Pyridine," *Acta Chem. Scand.* 20: pp. 1561-1570 (1966) No. 6.

*Primary Examiner*—Henry R. Jiles
*Assistant Examiner*—Bernard I. Dentz
*Attorney, Agent, or Firm*—Gerald L. Coon

[57] ABSTRACT

2,3-Dihydro-2,2-dimethyl-7-hydroxybenzofuran is prepared by reacting catechol with isobutylene oxide or with a compound having the general formula

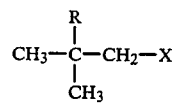

wherein R is halogen or hydroxyl, and X is halogen, in the presence of a base to form the intermediate 2-(2-hydroxy-2-methylpropoxy) phenol and then thermally dehydrating, rearranging and cyclizing the resulting intermediate phenol in the presence of an acid catalyst to form 2,3-dihydro-2,2-dimethyl-7-hydroxybenzofuran.

17 Claims, No Drawings

INTERMEDIATE, ITS SYNTHESIS, AND ITS USE IN A PROCESS FOR THE PREPARATION OF 2,3-DIHYDRO-2,2-DIMETHYL-7-HYDROXYBENZOFURAN

FIELD OF THE INVENTION

This invention relates to a process for the preparation of 2,3-dihydro-2,2-dimethyl-7-hydroxybenzofuran from catechol. More particularly, this invention involves a process for the mono-alkylation of catechol to produce 2-(2-hydroxy-2-methylpropoxy)phenol, a novel intermediate product, and its subsequent conversion to 2,3-dihydro-2,2-dimethyl-7-hydroxybenzofuran.

BACKGROUND OF THE INVENTION 2,3-Dihydro-2,2-dimethyl-7-hydroxybenzofuran (hereinafter also referred to as carbofuran phenol),

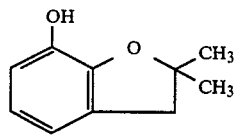

is a known compound useful as an intermediate in the synthesis of 2,3-dihydro-2,2-dimethyl-benzofuranyl methylcarbamate, a well known insecticide known by its accepted generic name carbofuran.

Known methods for preparation of carbofuran phenol from catechol generally involve alkylation of catechol with methallyl halide and subsequent thermal rearrangement and cyclization of the resulting 2-methallyloxyphenol to form carbofuran phenol. Disclosures and details of the steps involved in this process are set forth in U.S. Pat. Nos. 3,474,170; 3,927,118; 4,314,086; 4,321,204 and 4,380,654.

An alternative method for the preparation of carbofuran phenol by thermally rearranging 2-isopropyl-1,3-benzodioxole is set forth in U.S. Pat. No. 4,118,400.

Gripenberg and Hase, *Acta Chem Scand.* 20, 1561-1570 (1966), report an acid-catalyzed thermal dehydration, rearrangement and cyclization of 2-hydroxy-2-methylpropoxybenzene to form 2,3-dihydro-2,2-dimethylbenzofuran.

Although (hydroxy-alkoxy phenols, such as 2-(2-methylpropoxy)phenol, which are homologous to the novel 2-(2-hydroxy-2-methylpropoxy)phenol of this invention are known, the known compounds are not capable of being converted to carbofuran phenol.

It is an object of the present invention to provide a new process for the preparation of carbofuran phenol. It is also the object of this invention to provide a novel intermediate for the preparation of carbofuran phenol. In particular, it is an object of this invention to provide a 2-(2-hydroxy-2-methylpropoxy)phenol which can be converted to carbofuran phenol.

DESCRIPTION OF THE INVENTION

This invention relates to a method for the preparation of 2,3-dihydro-2,2-dimethyl-7-hydroxybenzofuran from catechol. This method proceeds according to the following general reaction scheme:

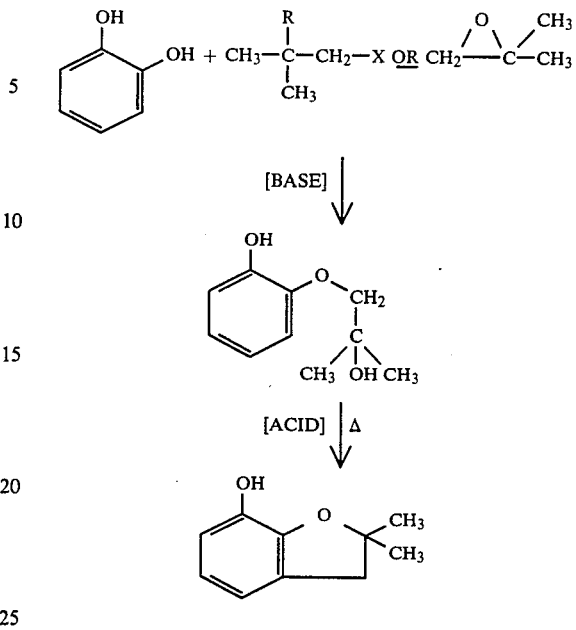

wherein R is halogen or hydroxyl and X is halogen. The method comprises alkylating catechol either with a hydroxy or halo substituted 1-(2-methylpropyl)halide or with isobutylene oxide, in the presence of a base and preferably a solvent, to form the intermediate 2-(2-hydroxy-2-methylpropoxy)phenol; and thereafter subjecting the resulting intermediate phenol to thermal dehydration, rearrangement and cyclization in the presence of an acid catalyst to produce carbofuran phenol.

The alkylation step can be conducted in the presence of any inorganic or organic base which is strong enough to abstract an acidic proton from catechol, which has a pKa of approximately 10. Suitable bases include alkali metal and alkaline earth metal hydroxides, oxides, carbonates and bicarbonates and basic ion exchange resins. Preferred bases include sodium carbonate, potassium carbonate and sodium hydroxide. The pH of the reaction mixture is preferably greater than about 9.

Neutral or basic solvents can be used in the alkylation step. Suitable solvents include aliphatic alcohols; polyhydroxyl ethers with at least one hydroxyl group; and basic organic solvents. Preferred solvents include methanol, 2-methoxyethanol, 2-ethoxyethanol and triethylamine. Aprotic solvents and inert organic solvents can also be used.

The temperature and pressure of the alkylation reaction are not critical. The reaction can be conducted at room temperature but elevated temperatures, preferably in the range of from about 60° C. to about 150° C. can be used if reduced reaction time is desired. Alkylation of catechol at temperatures greater than about 100° C. produces not only 2-(2-hydroxy-2-methylpropoxy)phenol but also 2-methallyloxyphenol, a known intermediate in the synthesis of carbofuran phenol. These two end products need not be separated for subsequent conversion to carbofuran phenol. The mixture of the two end products can be converted to carbofuran phenol by the procedure described below for conversion of 2-(2-hydroxy-2-methylpropoxy)phenol alone.

The reaction is preferably conducted at atmospheric pressure but can be conducted at sub-atmospheric or super-atmospheric pressure.

Catechol is preferably O-alkylated with 1,2-dichloro-2-methylpropane or with 1-chloro-2-methyl-2-propanol in the presence of a base and a solvent in an environment with a pH greater than about 9 to produce the novel intermediate phenol, 2-(2-hydroxy-2-methylpropoxy)phenol.

Most preferably, catechol is O-alkylated with 1,2-dichloro-2-methyl-propane in the presence of sodium carbonate and 2-ethoxyethanol in an environment with a pH greater than about 9 to product the novel intermediate phenol.

The resulting intermediate 2-(2-hydroxy-2-methylpropoxy)phenol is thermally dehydrated, rearranged and cyclized to form carbofuran phenol by heating the intermediate phenol in the presence of an acid catalyst at a temperature greater than about 90° C., preferably greater than about 110° C., and preferably at atmospheric pressure. This step can be conducted at sub-atmospheric or super-atmospheric pressure if desired.

The acid catalyst can be an organic acid, a non-aqueous inorganic acid or an aqueous inorganic acid in the presence of a phase transfer agent. Suitable acid catalysts include organic acids, Lewis acids, sulfonic acids and acidic ion exchange resins containing sulfonic acid groups. Preferred acid catalysts include pyridine hydrochloride and para-toluenesulfonic acid. The reaction proceeds in a strongly acidic environment, preferably in the range of from about pH 0.5 to 3, and most preferably from about pH 1 to 2.

No solvent is required for this step but, if desired, the reaction can be conducted in the presence of a non-basic organic solvent, preferably an inert organic solvent.

Preferably, in this step, the intermediate 2-(2-hydroxy-2-methylpropoxy)phenol is combined with para-toluensulfonic acid and toluene and heated to reflux (approximately 111° C.) to produce carbofuran phenol.

In an alternate and most preferred embodiment, the intermediate 2-(2-hydroxy-2-methylpropoxy)phenol is combined with pyridine hydrochloride and heated to reflux (approximately 222° C.) in the absence of any solvent to produce carbofuran phenol.

The following examples are provided to more clearly illustrate the invention:

EXAMPLE 1

Preparation of 2-(2-hydroxy-2-methylpropoxy)phenol from 1-chloro-2-methyl-2-propanol Catechol (11.0 g, 0.10 mole), sodium carbonate (10.6 g, 0.10 mole) and 100 g methanol were combined in a 250 ml 3-necked round bottom flask equipped with an air stirrer, heating mantle, condenser and thermometer, and heated to reflux (approximately 65° C.). 1-Chloro-2-methyl-2-propanol (10.9 g, 0.10 mole) was added by syringe. The mixture was refluxed for 3 hours, then left standing overnight. Water (40 ml) was added and the mixture was refluxed for 2 hours. After cooling, the water was extracted three times with 100 ml of dichloromethane. The combined dichloromethane layers were washed twice with 100 ml of water, then concentrated to afford 4.40 g (24%) of waxy yellow solid. Recrystallization from ethyl acetate (10 g) and hexane (50 g) gave a white solid. $^1$Hnmr analysis was consistent with the structural formula of 2-(2-hydroxy-2-methylpropoxy)phenol.

Analysis: Cald., C 65.91%, H, 7.74%; found, C 65.85, 66.05, H 7.66, 7.66.

EXAMPLE 2

Preparation of 2-(2-hydroxy-2-methylpropoxy)phenol from 1,2-dichloro-2-methylpropane Catechol (22.0 g, 0.20 mole), sodium carbonate (23.3 g, 0.22 mole), 1,2-dichloro-2-methylpropane (48 g, 0.30 mole), and 160 ml 2-ethoxyethanol were combined in a 500 ml 3-necked round bottom flask equipped with an air stirrer, thermometer, nitrogen inlet, heating mantle and condenser. The flask was flushed with nitrogen, then heated at 85°–95° C. for 5 hours. The reaction was cooled, then acidified with 150 ml of 10% aqueous sulfuric acid. Water (250 ml) was added and the mixture was extracted three times with 150 ml diethyl ether. Concentration of the combined ether layers afforded 26.2 g orange solid, which was mostly catechol. The solid was partitioned between 200 ml water and 200 ml of dichloromethane. The dichloromethane layer was washed five times with 100 ml of water to remove residual catechol. Concentration of the dried dichloromethane layers afforded 6.4 g (18%) orange solid, which was recrystallized from toluene. This gave pale yellow crystals, m.p. 107°–108° C. $^1$Hnmr analysis and mass spctral analysis were consistent with the structural formula of 2-(2-hydroxy-2-methylpropoxy)phenol.

EXAMPLE 3

Preparation of 2-(2-hydroxy-2-methylpropoxy)phenol and 2-methallyloxyphenol from 1,2-dichloro-2-methylpropane Catechol (11.0 g, 0.10 mole) and 80 ml of 2-methoxyethanol were combined in a 250 ml flask equipped with an air stirrer, thermometer, nitrogen inlet, heating mantle and condenser. Sodium hydroxide (4.0 g, 0.10 mole) was added gradually and then the mixture was refluxed for 0.5 hours (124° C.) 1,2-Dichloro-2-methylpropane (19.1 g, 0.15 mole) was added and the mixture was refluxed for 5 hours (124° C.). The mixture was cooled and left standing overnight. Water (150 ml), acidified with hydrochloric acid, was added and the mixture was extracted five times with 75 ml of dichloromethane. The combined dichloromethane layers were washed with water, dried over magnesium sulfate and filtered. Gas-liquid chromatography analysis showed that 75% of the catechol remained, 16% was converted to 2-methallyloxyphenol and 9% was converted to 2-(2-hydroxy-2-methylpropoxy)phenol.

EXAMPLE 4

Preparation of 2-(2-hydroxy-2-methylpropoxy)phenol from isobutylene oxide

Catechol (7.7 g, 0.07 mole), isobutylene oxide (5.0 g, 0.069 mole), sodium carbonate (11.1 g, 0.015 mole) and 2-methoxyethanol (25 ml) were combined in a 125 ml three-necked round bottom flask equipped with reflux condenser, nitrogen inlet, thermometer, air-driven stirrer and heating mantle. The mixture was heated at 90° C. for 5 hours under a nitrogen blanket and then cooled. GLC analysis showed that approximately 50% of the catechol was converted to 2-(2-hydroxy-2-methylpropoxy)phenol.

EXAMPLE 5

Preparation of 2,3-dihydro-2,2-dimethyl-7-hydroxybenzofuran (solventless)

2-(2-Hydroxy-2-methylpropoxy)phenol (2.47 g, 0.0136 mole) and solid pyridine hydrochloride (8.0 g, 0.069 mole) were combined and heated to reflux (222° C.) for one hour. After cooling, the mixture was diluted with water and extracted three times with 50 ml of dichloromethane. The combined dichloromethane layers were concentrated to give 0.81 g of a dark oil. $^1$Hnmr analysis showed the presence of 2,3-dihydro-2,2-dimethyl-7-hydroxybenzofuran, pyridine and 2-(2-Hydroxy-2-methylpropoxy)phenol.

EXAMPLE 6

Preparation of 2,3-dihydro-2,2-dimethyl-7-hydroxybenzofuran in toluene 2-(2-hydroxy-2-methylpropoxy)phenol (0.2 g, 1.1 mmole), a catalytic amount of para-toluenesulfonic acid and 10 ml of toluene were combined in a single-necked 50 ml round bottom flask equipped with a magnetic stirrer, reflux condenser, Dean-Stark trap and heating mantle. The mixture was heated to reflux (111° C.) with stirring. Water appeared in the Dean-Stark trap almost immediately. The mixture was cooled and analyzed by GLC. The analysis confirmed the presence of 2,3-dihydro-2,2-dimethyl-7-hydroxybenzofuran.

What is claimed is:

1. A process for the preparation of 2-(2-hydroxy-2-methylpropoxy)phenol which comprises reacting catechol with an alkylating agent of the formula:

wherein Q is

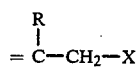

wherein R is halogen and X is halogen;
in the presence of a base and a solvent in an environment with a pH greater than about 9 to form 2-(2-hydroxy-2-methylpropoxy)phenol.

2. A process as recited in claim 1 wherein said alkylating agent is 1,2-dichloro-2-methylpropane.

3. A process as recited in claim 1 wherein said base is an alkali metal hydroxide, oxide, carbonate or bicarbonate; an alkaline earth metal hydroxide, oxide, carbonate or bicarbonate; or a basic ion exchange resin.

4. A process as recited in claim 1, wherein said base is sodium carbonate or sodium hydroxide.

5. A process as recited in claim 1 wherein said solvent is an inert organic solvent.

6. A process as recited in claim 1, conducted in the presence of a neutral or basic solvent.

7. A process as recited in claim 6, wherein said neutral or basic solvent is an aliphatic alcohol; a polyhydroxyl ether with one or more hydroxyl groups; an aprotic solvent; or a basic organic solvent.

8. A process as recited in claim 6, wherein said neutral or basic solvent is methanol, 2-methoxyethanol, 2-ethoxyethanol, or triethylamine.

9. 2-(2-Hydroxy-2-methylpropoxy)phenol.

10. A process for the preparation of 2,3-dihydro-2,2-dimethyl-7-hydroxybenzofuran which comprises:

(a) reacting catechol with an alkylating agent of the formula:

wherein Q is

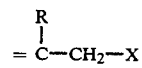

wherein R is halogen and X is halogen;
in the presence of a base and a solvent in an environment with a pH greater than about 9 to form 2-(2-hydroxy-2-methylpropoxy)phenol; and (b) heating the resultant 2-(2-hydroxy-2-methylpropoxy)phenol in the presence of an acid catalyst at a temperature greater than about 90° C. to form the 2,3-dihydro-2,2-dimethyl-7-hydroxybenzofuran.

11. A process as recited in claim 10 wherein said alkylating agent is 1,2-dichloro-2-methylpropane.

12. A process as recited in claim 10, wherein said base is an alkali metal hydroxide, oxide, carbonate or bicarbonate; an alkaline earth metal hydroxide, oxide, carbonate or bicarbonate; or a basic ion exchange resin.

13. A process as recited in claim 10 wherein said acid catalyst is an organic acid, a Lewis acid, a sulfonic acid or an acidic ion exchange resin containing sulfonic acid groups 14. A process as recited in claim 10 wherein step (b) is conducted at a temperature greater than about 110° C.

15. A process as recited in claim 10 wherein step (b) is conducted in the presence of a non-biasic organic solvent.

16. A process as recited in claim 10 wherein step (b) is conducted in the absence of a solvent.

17. A process as recited in claim 10 wherein step (b) is conducted over a pH range of from about 1 to 2.

* * * * *